_(12)_ United States Patent
Hu et al.

(10) Patent No.: US 10,377,728 B2
(45) Date of Patent: Aug. 13, 2019

(54) METHOD FOR PREPARING 2,5-DIMETHYLFURAN BY DIRECTLY CATALYZING CARBOHYDRATE USING MODIFIED PD/C

(71) Applicant: Guizhou University, Guiyang, Guizhou (CN)

(72) Inventors: Li Hu, Guiyang (CN); Yang Song, Guiyang (CN); Zhao Wenfeng, Guiyang (CN); Xue Wei, Guiyang (CN); Fang Zhen, Guiyang (CN)

(73) Assignee: GUIZHOU UNIVERSITY, Guiyang (CN)

( * ) Notice: Subject to any disclaimer, the term of this patent is extended or adjusted under 35 U.S.C. 154(b) by 0 days.

(21) Appl. No.: 16/313,203

(22) PCT Filed: Oct. 12, 2017

(86) PCT No.: PCT/CN2017/105835
§ 371 (c)(1),
(2) Date: Dec. 26, 2018

(87) PCT Pub. No.: WO2018/157604
PCT Pub. Date: Sep. 7, 2018

(65) Prior Publication Data
US 2019/0152936 A1 May 23, 2019

(30) Foreign Application Priority Data
Mar. 2, 2017 (CN) .......................... 2017 1 0119440

(51) Int. Cl.
| | |
|---|---|
| *C07D 307/36* | (2006.01) |
| *B01J 23/44* | (2006.01) |
| *B01J 37/20* | (2006.01) |
| *B01J 31/02* | (2006.01) |
| *B01J 31/28* | (2006.01) |
| *B01J 21/18* | (2006.01) |

(52) U.S. Cl.
CPC ............ *C07D 307/36* (2013.01); *B01J 23/44* (2013.01); *B01J 31/0274* (2013.01); *B01J 31/28* (2013.01); *B01J 37/20* (2013.01); *B01J 21/18* (2013.01)

(58) Field of Classification Search
CPC ......... C07D 307/36; B01J 37/20; B01J 23/44; B01J 21/18; B01J 31/0274; B01J 31/28
See application file for complete search history.

(56) References Cited

U.S. PATENT DOCUMENTS

| 2011/0184195 A1 | 7/2011 | Lange et al. | |
|---|---|---|---|
| 2011/0263880 A1* | 10/2011 | Rauchfuss | ........... C07D 307/36 549/506 |

FOREIGN PATENT DOCUMENTS

| CN | 101434588 A | 5/2009 |
|---|---|---|
| CN | 102089292 A | 6/2011 |
| CN | 105013538 A | 11/2015 |
| CN | 106861754 A | 6/2017 |
| WO | 2015031753 A1 | 3/2015 |

OTHER PUBLICATIONS

Marriam-Webster Dictionary 2018 https://www.merriam-webster.com/dictionary/tild; p. 1-9.*
International Search Report dated Jan. 23, 2018, issued in counterpart application No. PCT/CN2017/105835 (3 pages).
Roman-Leshkov et al., "Production of dimethylfuran for liquid fuels from biomass-derived carbohydrates", Nature, Jun. 2007, vol. 447, pp. 982-985, (6 pages).
Cheng et al., "Production of targeted aromatics by using Diels-Alder classes of reactions with furans and olefins over ZSM-5", Green Chemistry, 2012, 14, pp. 3114-3125, (12 pages).
Hu et al., "Chemoselective Hydrogenation of Biomass-Derived 5-Hydroxymethylfurfural into the Liquid Biofuel 2,5-Dimethylfuran", Industrial & Engineering Chemistry Research, ACS publications, 2014, 53, pp. 9969-9978, (10 pages).
Kazi et al., "Techno-economic analysis of dimethylfuran (DMF) and hydroxymethylfurfural (HMF) production from pure fructose in catalytic processes", Chemical Engineering Journal, Elsevier, 2011, 169, pp. 329-338, (10 pages).
Senapati, "Polymethylhydrosiloxane (PMHS)", Spotlight 129, SYNLETT, 2005, No. 12 pp. 1960-1961, (2 pages).
Volkov et al., "Mild Deoxygenation of Aromatic Ketones and Aldehydes over Pd/C Using Polymethylhydrosiloxane as the Reducing Agent**", Angewandte Chemie International Edition, 2015, 127, pp. 5211-5215, (5 pages).
De et al., "One-Pot Conversions of Lignocellulosic and Algal Biomass into Liquid Fuels", ChemSusChem, 2012, 5, pp. 1826-1833, cited in ISR (8 pages).
Hu et al., "Selective Transformation of 5-Hydroxymethylfurfural into the Liquid Fuel 2,5-Dimethylfuran over Carbon-Supported Ruthenium", Industrial & Engineering Chemistry Research, ACS Publications, 2014, 53, pp. 3056-3064, cited in ISR (9 pages).

* cited by examiner

*Primary Examiner* — John M Mauro
(74) *Attorney, Agent, or Firm* — Westerman, Hattori, Daniels & Adrian, LLP

(57) ABSTRACT

A preparation method of an acidic and hydrophobic Pd/C catalytic material comprises performing a simple treatment with chlorosulfonic acid and trimethylchlorosilane, washing and drying a treatment product to obtain a modified Pd/C catalytic material. A method for preparing 2,5-methylfuran by catalyzing a carbohydrate with modified Pd/C comprises: dissolving the carbohydrate in alcohol, allowing a reaction to proceed with modified Pd/C as a catalyst and polymethylhydrosiloxane as a hydrogen donor at a temperature of 80~140° C. for 1-5 hours, and performing centrifugation to separate the catalyst from the product. The content of the modified Pd/C content is 1-3 mol % relative to the carbohydrate; the polymethylhydrosiloxane amount is equivalent to 4-10 times the carbohydrate amount, and the carbohydrate concentration in the alcohol is 2-6 wt %. The method overcomes the defect of being difficult to prepare the 2,5-methylfuran by directly catalyzing the carbohydrate, and features moderate reaction conditions and high activity.

10 Claims, 2 Drawing Sheets

METHOD FOR PREPARING 2,5-DIMETHYLFURAN BY DIRECTLY CATALYZING CARBOHYDRATE USING MODIFIED PD/C

BACKGROUND OF THE INVENTION

Technical Field

The present disclosure relates to a method for preparing 2,5-methylfuran by directly catalyzing carbohydrates with modified Pd/C. Specifically speaking, Pd/C modified with chlorosulfonic acid and trimethylchlorosilane is used to catalyze a biomass sugar source (hexose monosaccharide or polysaccharide to obtain 2,5-methylfuran by a "one-pot-one-step" process under the condition of employing polymethylhydrosiloxane as a hydrogen donor.

Description of Related Art

Along with the rapid development of the world economy and society, the global petrochemical resource consumption increases day by day. Petroleum prices rise continuously and fuel supply faces increasing challenges. Besides, waste gases (for example, sulfur oxide, nitric oxide, $CO_2$ and CO) discharged after combustion of petroleum and coals will cause environmental pollution or greenhouse effect, worsening the ecological environment. Therefore, bio-fuel as a novel, environmentally-friendly and alternative green energy has become a key research subject and hotspot of people engaged with scientific research. Particularly, 2,5-methylfuran has a energy density (31.5 kJ/mol) very close to that (35 kJ/mol) of gasoline, and has a higher hexadecyl value than the gasoline has (RON: 119>90-100)[1]. In addition, 2,5-methylfuran has a great application prospect[2] in the preparation of fine chemicals (for example, dimethyl benzene).

The traditional preparation method of the 2,5-methylfuran usually adopts 5-hydroxymethylfurfural, a downstream platform molecule of hexose, as a raw material, and employs a catalysis system that is usually a Ru, Pd, Pt, Ni or Cu-based single metallic catalyst, taking an acidic medium or a carrier and hydrogen molecule as a hydrogen donor[3]. The above-mentioned system can obtain a higher 2,5-methylfuran yield, but still have many disadvantages such as complicated process, high cost, and strict reaction conditions. Replacing the 5-hydroxymethylfurfural with carbohydrates as the raw material has the advantages of low raw material price, environmental protection and sustainable development. However, a catalysis process usually has various defects[4], for example, involving in two or more-step processes, complication in production distribution, and needs to separate and purify reactive intermediates to continue the next conversion reaction. Thus, the research and manufacturing of catalytic materials or systems with high activity and selectivity is critical for the direct efficient catalysis of carbonhydrates for preparation of the 2,5-methylfuran and the realization of corresponding industrial production.

Polymethylhydrosiloxane is a side product obtained during the industrial production of organosilicone, having features[5] of being non-toxic, low in price, safe in use and stable in air and water. In the organic synthesis field, polymethylhydrosiloxane is usually used as a hydrogen donor to catalyze the reducing reaction of amides, esters, hydroxy, nitryl and carbonyl compounds, etc., by the effect of a single metallic substance (in particular Pd). Usually, direct catalysis of sugars (in particular polysaccharides) into the 2,5-methylfuran involves reaction processes such as hydrolysis, dehydration and hydrogenation. Therefore, how to effectively control the catalyst structure and catalysis system composition to implement the above-mentioned "one-pot-one-step" selective series-connection multiple reactions is a key for the preparation of the 2,5-methylfuran at a high yield. However, no relevant literature and patent is found yet.

[1] Roman-Leshkov, Y.; Barrett, C. J.; Liu, Z. Y.; Dumesic, J. A. "Production of dimethylfuran for liquid fuels from biomass-derived carbohydrates." Nature, 2007, 447, 982-985.

[2] Cheng, Y. T.; Huber, G. W. "Production of targeted aromatics by using Diels-Alder classes of reactions with furans and olefins over ZSM-5." Green Chemistry, 2012, 14, 3114-3125.

[3] Hu, L.; Lin, L.; Liu, S. "Chemoselective hydrogenation of biomass-derived 5-hydroxymethylfurfural into the liquid biofuel 2,5-dimethylfuran." Industrial & Engineering Chemistry Research, 2014, 53, 9969-9978.

[4] Kazi, F. K.; Patel, A. D.; Serrano-Ruiz, J. C.; Dumesic, J. A.; Anex, R. P. "Techno-economic analysis of dimethylfuran (DMF) and hydroxymethylfurfural (HMF) production from pure fructose in catalytic processes." Chemical Engineering Journal, 2011, 169, 329-338.

[5] Senapati, K. K. Polymethylhydrosiloxane (PMHS). Synlett, 2005, 2005, 1960-1961.

[6] Volkov, A.; Gustafson, K. P.; Tai, C. W.; Verho, O.; Bäckvall, J. E.; Adolfsson, H. "Mild deoxygenation of aromatic ketones and aldehydes over Pd/C using polymethylhydrosiloxane as the reducing agent." Angewandte Chemie International Edition, 2015, 54, 5122-5126.

BRIEF SUMMARY OF THE INVENTION

The objective of the present disclosure is to provide a method for effectively preparing 2,5-methylfuran by directly catalyzing carbohydrates. The method is moderate in process conditions, high in reaction rate and wide in applicable primer range, and can overcome defects of high energy consumption, high cost and strict reaction conditions of the prior art.

To achieve the above objective, the present disclosure adopts the following technical solution: A method for preparing 2,5-methylfuran by directly catalyzing carbohydrates with modified Pd/C, characterized by including the following steps:

Step 1: preparation of the modified Pd/C: homogeneously dispersing 0.5 g of Pd/C into 15 mL of methylene dichloride, slowly dropping 0.05-0.35 mL of chlorosulfonic acid with stirring to obtain a mixed substance, continuously stirring the mixed substance for 12 hours at room temperature, then filtering the mixed substance, washing the mixed substance with methylene dichloride and water repeatedly until filtrate is neutral, drying a product obtained after filtration in vacuum at a temperature of 90° C. for 6 hours to obtain an acidic Pd/C catalytic material; placing 0.25 g of the obtained acidic Pd/C catalytic material in 7.5 mL of cyclohexane, adding 1.5 mL of trimethylchlorosilane drop by drop to obtain a mixture, heating the mixture to a temperature of 60° C. and stirring the mixture for 12 hours at the temperature of 60° C. to make sure that a reaction proceeds; after the reaction ends, washing a reaction product using n-hexane for 5 times, drying the washed product in vacuum at a temperature of 90° C. for 6 hours to obtain a dried product, and grinding the dried product to obtain the modified Pd/C;

Step 2: dissolving carbohydrates into alcohol, and allowing a reaction to proceed at a temperature of 80~140° C. for 1-5 hours by taking the modified Pd/C obtained in step (1) as a catalyst and polymethylhydrosiloxane as a hydrogen donor; and after the reaction ends, performing a centrifugation operation to separate the catalyst from the obtained reaction product to obtain the 2,5-methylfuran.

According to the present disclosure, the modified Pd/C catalytic material is an acidic and hydrophobic Pd/C catalytic material, modified Pd/c in short, prepared by steps of treating commercially available Pd/C with chlorosulfonic acid and trimethylchlorosilane in turn, washing the treated product with n-hexane, drying the washed product in vacuum, and grinding the dried product.

According to the present disclosure, the amount of the polymethylhydrosiloxane is equivalent to 4-10 times the amount of the carbohydrates used.

According to the present disclosure, the concentration of the carbohydrates in alcohol is 2-6 wt %.

In the present disclosure, a reactor used for preparing the catalyst is a 50 mL round-bottom flask.

According to the present disclosure, the stirring conditions include magnetic stirring, and 600 r/min rotation speed.

According to the present disclosure, the amount of the chlorosulfonic acid used is 0.20 mL, and the slow dropping time is 2 min.

According to the present disclosure, washing is carried out with the n-hexane for five times, and the amount of the n-hexane is 20 mL each time.

The present disclosure also provides an application of the modified Pd/C in the preparation of the 2,5-methylfuran by directly catalyzing carbohydrates.

Preferably, the reaction time is 100~-120° C., and the reaction time is 1-3 hours.

Preferably, the content of the modified Pd/C is 1-3 mol % relative to the carbohydrates; the amount of the polymethylhydrosiloxane is equivalent to 6-9 times the amount of the carbohydrates used; and the concentration of the carbohydrates in the alcohol is 3-5 wt %.

According to the present disclosure, the carbohydrates are common hexose, including fructose, glucose, maltose, saccharose, cellose, starch, synanthrin or cellulose.

The alcohol is methanol, ethanol, n-propanol, n-butanol or n-hexanol.

As an preferred solution of the method for preparing 2,5-methylfuran by directly catalyzing carbohydrates, regeneration of a modified Pd/C catalyst is also comprised: the catalyst is filtered out from the reaction liquid, washed for 4-6 times respectively with the ethanol and the n-hexane, dried at a temperature of 90° C. for 5-12 hours, and then ground to obtain the regenerated catalyst.

Compared with the prior art, the present disclosure has the following beneficial effects:

(1) The catalytic material of the present disclosure is simple in the preparation method, is made of easily accessible raw materials, has high hydrophobicity, and contains acid-metal dual-functional sites;

(2) The modified Pd/C of the present disclosure has high catalytic activity and is easily separated and recycled;

(3) The modified Pd/C of the present disclosure is widely applicable to different carbohydrates, and also has the advantages of moderate reaction conditions, high selectivity, stability, reaction rate and reusability;

(4) Under the same condition, the efficiency of catalyzing the carbohydrates by the "one-pot-one-step" process using the modified Pd/C that is prepared by method of the present disclosure into the 2,5-methylfuran (yield>85%) is obvious higher than that of the commercially available Pd/C (<50%) and that of other metallic catalysts such as Co, Ni, Ru, Pt (0-30%).

DETAILED DESCRIPTION OF THE INVENTION

Embodiment 1

(1) Preparation of Modified 5 Wt % Pd/C

The preparation mainly involves the following two processes: (A) 0.5 g of 5 wt % Pd/C was weighed and added into 15 mL of methylene dichloride, and the mixed materials were stirred until they were homogeneously distributed. Next, 0.2 mL of chlorosulfonic acid was slowly dropped (about 2 min) to obtain a mixture; the mixture was stirred for 12 hours at room temperature, and then was filtered and repeatedly washed with methylene dichloride and water in turn until filtrate was neutral; a product obtained after the filtration was dried in vacuum at a temperature of 90° C. for 6 hours to obtain an acidic Pd/C catalytic material. (B) 0.25 g of the obtained acidic Pd/C catalytic material was weighed and placed in 7.5 mL of cyclohexane to obtain a mixed system; then, 1.5 mL of trimethylchlorosilane was slowly added into the mixed system drop by drop; after dropping, the obtained mixture was heated to a temperature of 60° C. and continuously stirred for 12 hours at the temperature of 60° C. to make sure that a reaction proceeded; after the reaction ends, the obtained reaction product was washed with n-hexane for 5 times, dried in vacuum at a temperature of 90° C. for 6 hours, and then ground to obtain the acidic and hydrophobic Pd/C catalytic material, namely the modified 5 wt % Pd/C.

Figure 1:
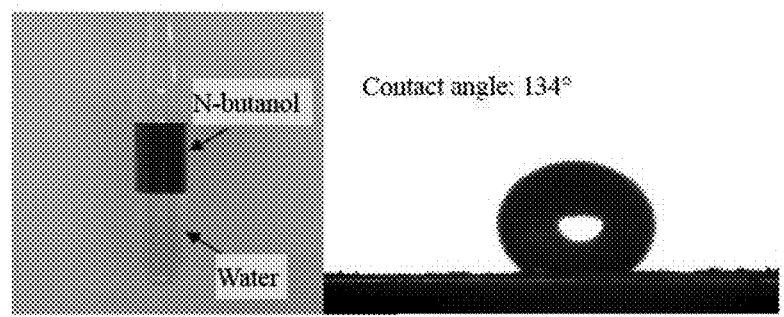
FIG. 1 shows the distribution of modified 5 wt % Pd/C in water and in butanol (left) and the contact angle of surface water drops (right)

From FIG. 1 it can be seen that the modified 5 wt % Pd/C was homogeneously dispersed in the n-butanol, but was basically separated from water (left figure); at the same time, a relatively large water drop contact angle (134°) also verified that the modified 5 wt % Pd/C had high hydrophobicity (right figure). Besides, an acid-base titration also verifies that the catalytic material has a relatively high acid content (~1.1 mmol/g). Thus, it can be judged that the modified 5 wt % Pd/C has relatively ideal hydrophobicity and acidity at the same time.

(2) Preparation of the 2,5-methylfuran by Directly Catalyzing Fructose 6 wt % fructose, 1.5 mL of n-butanol, 2 mol % modified 5 wt % Pd/C and 9 equivalent times (relative to the fructose) of polymethylhydrosiloxane were added into a 15 mL pressure-resistant glass reactor; the mixed materials were heated to a temperature of 80° C. and then stirred for 4 hours at the temperature of 80° C., or heated to a temperature of 120° C. and stirred for 1 hour at the temperature of 120° C. to make sure that a reaction proceeded. After the reaction ended, centrifugation was carried out to separate the solid catalyst, and the conversion rate of the fructose and the yield of the 2,5-methylfuran in the reaction liquid were respectively determined using HPLC (High Performance Liquid Chromatography) and GC (Gas Chromatography). Standard curves of corresponding standard solutions were prepared, and peak areas of samples to be measured were brought into the curves to obtain the conversion rate of the fructose and the yield of the 2,5-methylfuran, which were 96% and 88%, respectively.

Figure 3:
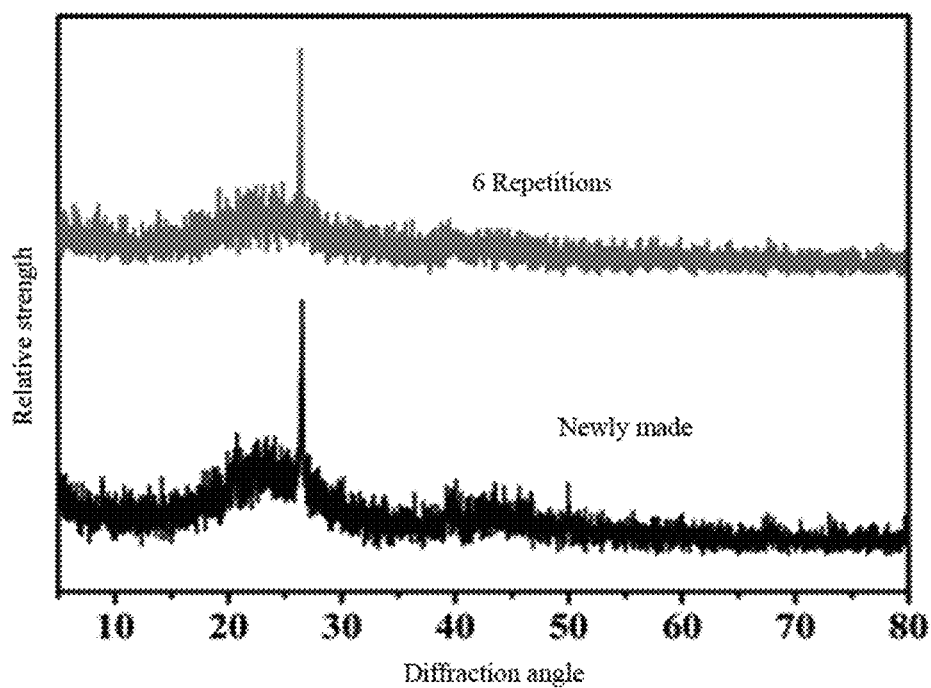
FIG. 3 is an XRD spectrogram obtained after the modified Pd/C is used for six times repeatedly (upper) and an XRD spectrogram of the modified Pd/C that is newly manufactured (lower).

(3) The solid catalyst obtained after filtration and separation was washed for 4-6 times respectively using ethanol and n-hexane, then dried at a temperature of 90° C. for 5-12 hours, and ground to obtain a regenerative catalyst; the regenerative modified 5 wt % Pd/C was used to directly catalyze the fructose to prepare the 2,5-methylfuran, wherein the amounts of the raw materials and the reaction conditions were respectively identical with those in Embodiment 1(2); liquid chromatography and gas chromatography were carried out to obtain the conversion rate of the fructose and the field of the 2,5-methylfuran in the reaction mixed liquid, which were 98% and 92%, respectively. Correspondingly, the almost the same XRD spectrograms (FIG. 3) obtained before and after the use of the modified 5 wt % Pd/C also well proved that the catalytic material had a stable structure.

Comparative Example 1

Figure 2:
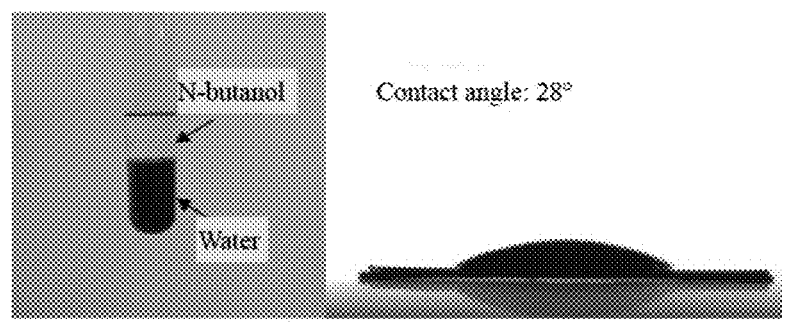
FIG. 2 shows the distribution of 5 wt % Pd/C in water and in butanol (left) and the contact angle of surface water drops (right)

5 wt % Pd/C used was a commercially available reagent, purchased from Beijing Innochem Scientific Co., Ltd. FIG. 2 shows that the 5 wt % Pd/C had good hydrophily (left figure), and a relatively low water drop contact angle (28°) also reflected that the material had an average hydrophobic ability.

The commercially available 5 wt % Pd/C obtained using such embodiment was used to catalyze fructose to prepare 2,5-methylfuran, and the amounts of all raw materials, reaction conditions, sample test methods were identical with those in Embodiment 1 (2). After the reaction ended, the conversion rate of the fructose and the yield of the 2,5-methylfuran in the mixed solution were measured through liquid and gas chromatography, which were 52% and 43%, respectively.

Correspondingly, 5 wt % Co/C, 5 wt % Ni/C, 5 wt % Ru/C and 5 wt % Pt/C were used to catalyze fructose under the same reaction conditions to prepare the 2,5-methylfuran, and the yields were 0, 0, 10% and 20%, respectively.

Embodiment 2

(1) Preparation of Modified 2 Wt % Pd/C

The preparation mainly involves the following two processes: (A) 0.5 g of 2 wt % Pd/C was weighed and added into 15 mL of methylene dichloride, and the mixed materials were stirred until they were homogeneously distributed. Next, 0.1 mL of chlorosulfonic acid was slowly dropped (about 1 min) to obtain a mixture; the mixture was stirred for 12 hours at room temperature, and then was filtered and repeatedly washed with methylene dichloride and water in turn until the filtrate was neutral; a product obtained after the filtration was dried in vacuum at a temperature of 90° C. for 6 hours to obtain an acidic Pd/C catalytic material. (B) 0.25 g of the obtained acidic Pd/C catalytic material was weighed and placed in 7.5 mL of cyclohexane to obtain a mixed system; then, 1.5 mL of trimethylchlorosilane was slowly added into the mixed system drop by drop; after dropping, the obtained mixture was heated to a temperature of 60° C. and continuously stirred for 12 hours at the temperature of 60° C. to make sure that a reaction proceeded; after the reaction ends, the obtained reaction product was washed with n-hexane for 5 times, dried in vacuum at a temperature of 90° C. for 6 hours, and then ground to obtain the acidic and hydrophobic Pd/C catalytic material, namely the modified 2 wt % Pd/C.

(2) Preparation of the 2,5-methylfuran by Directly Catalyzing Glucose 4 wt % glucose, 1.5 mL of n-hexanol, 1.5 mol % modified 2 wt % Pd/C and 5 equivalent times (relative to the glucose) of polymethylhydrosiloxane were added into a 15 mL pressure-resistant glass reactor; the mixed materials were heated to a temperature of 120° C. and stirred for 2 hours at the temperature of 120° C. to make sure that a reaction proceeded. After the reaction ended, centrifugation was carried out to separate the solid catalyst, and the conversion rate of the glucose and the yield of the 2,5-methylfuran in the reaction liquid were respectively determined using HPLC (High Performance Liquid Chromatography) and GC (Gas Chromatography). Standard curves of corresponding standard solutions were prepared, and peak areas of samples to be measured were brought into the curves to obtain the conversion rate of the glucose and the yield of the 2,5-methylfuran, which were 87% and 65%, respectively.

Embodiment 3

(1) Preparation of Modified 0.5 Wt % Pd/C

The preparation mainly involves the following two processes: (A) 0.5 g of 0.5 wt % Pd/C was weighed and added into 15 mL of methylene dichloride, and the mixed materials were stirred until they were homogeneously distributed. Next, 0.3 mL of chlorosulfonic acid was slowly dropped (about 3 min) to obtain a mixture; the mixture was stirred for 12 hours at room temperature, and then was filtered and repeatedly washed with methylene dichloride and water in turn until the filtrate was neutral; a product obtained after the filtration was dried in vacuum at a temperature of 90° C. for 6 hours to obtain an acidic Pd/C catalytic material. (B) 0.25 g of the obtained acidic Pd/C catalytic material was weighed and placed in 7.5 mL of cyclohexane to obtain a mixed system; then, 1.5 mL of trimethylchlorosilane was slowly added into the mixed system drop by drop; after dropping, the obtained mixture was heated to a temperature of 60° C. and continuously stirred for 12 hours at the temperature of 60° C. to make sure that a reaction proceeded; after the reaction ends, the obtained reaction product was washed with n-hexane for 5 times, dried in vacuum at a temperature of 90° C. for 6 hours, and then ground to obtain the acidic and hydrophobic Pd/C catalytic material, namely the modified 0.5 wt % Pd/C.

(2) Preparation of the 2,5-methylfuran by Directly Catalyzing Saccharose 4 wt % saccharose, 1.5 mL of ethanol, 3 mol % modified 0.5 wt % Pd/C and 10 equivalent times (relative to the saccharose) of polymethylhydrosiloxane were added into a 15 mL pressure-resistant glass reactor; the mixed materials were heated to a temperature of 100° C. and stirred for 5 hours at 100° C. to make sure a reaction proceeded. After the reaction ended, centrifugation was carried out to separate the solid catalyst, and the conversion rate of the saccharose and the yield of the 2,5-methylfuran in the reaction liquid were respectively determined using HPLC (High Performance Liquid Chromatography) and GC (Gas Chromatography). Standard curves of corresponding standard solutions were prepared, and peak areas of samples to be measured were brought into the curves to obtain the conversion rate of the saccharose and the yield of the 2,5-methylfuran, which were 95% and 83%, respectively.

Embodiment 4

(1) Preparation of Modified 15 Wt % Pd/C

The preparation mainly involves the following two processes: (A) 0.5 g of 15 wt % Pd/C was weighed and added into 15 mL of methylene dichloride, and the mixed materials were stirred until they were homogeneously distributed. Next, 0.15 mL of chlorosulfonic acid was slowly dropped (about 1.5 min) to obtain a mixture; the mixture was stirred for 12 hours at room temperature, and then was filtered and repeatedly washed with methylene dichloride and water in turn until the filtrate was neutral; a product obtained after the filtration was dried in vacuum at a temperature of 90° C. for 6 hours to obtain an acidic Pd/C catalytic material. (B) 0.25 g of the obtained acidic Pd/C catalytic material was weighed and placed in 7.5 mL of cyclohexane to obtain a mixed system; then, 1.5 mL of trimethylchlorosilane was slowly added into the mixed system drop by drop; after dropping, the obtained mixture was heated to a temperature of 60° C. and continuously stirred for 12 hours at the temperature of 60° C. to make sure that a reaction proceeded; after the reaction ends, the obtained reaction product was washed with n-hexane for 5 times, dried in vacuum at a temperature of 90° C. for 6 hours, and then ground to obtain the acidic and hydrophobic Pd/C catalytic material, namely the modified 15 wt % Pd/C.

(2) Preparation of the 2,5-methylfuran by Directly Catalyzing Synanthrin 2 wt % synanthrin, 1.5 mL of methanol, 1 mol % modified 15 wt % Pd/C and 6 equivalent times (relative to the synanthrin) of polymethylhydrosiloxane were added into a 15 mL pressure-resistant glass reactor; the mixed materials were heated to a temperature of 140° C. and stirred for 3 hours at 140° C. to make sure a reaction proceeded. After the reaction ended, centrifugation was carried out to separate the solid catalyst, and the conversion rate of the synanthrin and the yield of the 2,5-methylfuran in the reaction liquid were respectively determined using HPLC (High Performance Liquid Chromatography) and GC (Gas Chromatography). Standard curves of corresponding standard solutions were prepared, and peak areas of samples to be measured were brought into the curves to obtain the conversion rate of the synanthrin and the yield of the 2,5-methylfuran, which were 99% and 90%, respectively.

What is claimed is:

1. A method of preparing 2,5-dimethylfuran by directly converting carbohydrates in the presence of modified Pd/C, comprising:
heating a solution comprising the carbohydrates, the modified Pd/C as a catalyst, and a hydrogen donor to obtain the 2,5-methylfuran;
wherein the modified Pd/C is obtained by treating Pd/C with chlorosulfonic acid to obtain an acidic Pd/C catalytic material, and then reacting the acidic Pd/C catalytic material with trimethylchlorosilane.

2. The method of preparing 2,5-dimethylfuran by directly converting carbohydrates in the presence of modified Pd/C according to claim 1, wherein the modified Pd/C comprises a Pd content within a range of 0.5 wt % to 15 wt %.

3. The method of preparing 2,5-dimethylfuran by directly converting carbohydrates in the presence of modified Pd/C according to claim 1, wherein the hydrogen donor is polymethylhydrosiloxane.

4. The method of preparing 2,5-dimethylfuran by directly converting carbohydrates in the presence of modified Pd/C according to claim 3, wherein an amount of the polymethylhydrosiloxane is equivalent to 4 to 10 times by weight an amount of the carbohydrates used.

5. The method of preparing 2,5-dimethylfuran by directly converting carbohydrates in the presence of modified Pd/C according to claim 1, wherein the solution further comprises an alcohol as a solvent, and a concentration of the carbohydrates relative to the alcohol is about 2 wt % to about 6 wt %.

6. The method of preparing 2,5-dimethylfuran by directly converting carbohydrates in the presence of modified Pd/C according to claim 5, wherein the alcohol is methanol, ethanol, n-propanol, n-butanol or n-hexanol.

7. The method of preparing 2,5-dimethylfuran by directly converting carbohydrates in the presence of modified Pd/C according to claim 1, wherein the carbohydrates are hexose.

8. The method of preparing 2,5-dimethylfuran by directly converting carbohydrates in the presence of according to claim 7, wherein the hexose includes fructose, glucose, maltose, saccharose, cellose, starch, synanthrin or cellulose.

9. The method of preparing 2,5-dimethylfuran by directly converting carbohydrates in the presence of modified Pd/C according to claim 1, wherein heating the solution is performed at a temperature in a range of about 80° C. to about 140° C. for a time in a range of about 1 to about 5 hours.

10. The method of preparing 2,5-dimethylfuran by directly converting carbohydrates in the presence of modified Pd/C according to claim 1, wherein treating Pd/C with chlorosulfonic acid to obtain the acidic Pd/C catalytic material comprises:
dispersing Pd/C in methylene dichloride to obtain a Pd/C dispersion, and
reacting the Pd/C dispersion with chlorosulfonic acid at room temperature to obtain the acidic Pd/C catalytic material.

* * * * *